United States Patent
Hayakawa et al.

(10) Patent No.: US 6,372,357 B1
(45) Date of Patent: Apr. 16, 2002

(54) EXTERNAL COMPONENT OF ENDOSCOPE

(75) Inventors: Shinji Hayakawa, Saitama; Rensuke Adachi; Kunitoshi Ikeda, both of Tokyo; Masanao Abe, Saitama, all of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/666,840

(22) Filed: Sep. 21, 2000

(30) Foreign Application Priority Data

Sep. 22, 1999 (JP) .................................... 11-267930

(51) Int. Cl.⁷ .............................. B32B 9/00; A61B 1/00
(52) U.S. Cl. .................... 428/472.2; 205/171; 205/172; 205/173; 205/317; 205/324; 205/327; 205/328; 205/332; 427/402; 427/407.1; 427/409; 427/419.2; 428/628; 428/629; 428/632; 428/650; 428/402; 428/403; 428/407; 428/926; 428/935; 600/101; 600/133; 600/140; 600/920

(58) Field of Search ............................ 428/472.2, 628, 428/629, 632, 650, 402, 926, 935, 403, 407; 427/402, 407.1, 409, 419.2; 205/171, 172, 173, 317, 324, 327, 328, 332; 600/101, 133, 140, 920

(56) References Cited

U.S. PATENT DOCUMENTS 5,599,278 A * 2/1997 Hibbard ...................... 600/133

FOREIGN PATENT DOCUMENTS

| JP | 7163511 | 6/1995 |
| JP | 8277476 | 10/1996 |
| JP | 8308788 | 11/1996 |
| JP | 83111695 | 11/1996 |

* cited by examiner

Primary Examiner—Robert R. Koehler
(74) Attorney, Agent, or Firm—Greenblum & Bernstein P.L.C.

(57) ABSTRACT

An external component of an endoscope includes an aluminum alloy base member whose surface is subjected to anodic oxidation, and thereafter, is subjected to an electrolytic deposition thereon.

7 Claims, 3 Drawing Sheets

Fig.1

| Used Liquid Medicament | Embodiment 1 | Embodiment 2 | Embodiment 3 | Embodiment 4 | Embodiment 5 | Embodiment 6 | Embodiment 7 | Embodiment 8 |
|---|---|---|---|---|---|---|---|---|
| Hydrogen Peroxide (8%) | Detenoration by 5% at 450 cycles No Functional Deterioration | Detenoration by 5% at 450 cycles No Functional Deterioration | Detenoration by 5% at 450 cycles No Functional Deterioration | Detenoration by 5% at 450 cycles No Functional Deterioration | Detenoration by 5% at 450 cycles No Functional Deterioration | Detenoration by 5% at 450 cycles No Functional Deterioration | Detenoration by 5% at 450 cycles No Functional Deterioration | Detenoration by 5% at 450 cycles No Functional Deterioration |
| Peracetic Acid (0.8%) | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Peroxide Disinfectant (10%) | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Peroxide Surface-active Agent (5%) | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Enzyme Washing Agent (10%) | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Ethylene Oxide Gas | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Iodic Disinfectant (10%) | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Alcohol Disinfectant (85vol%) | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Overall Judgement | ○ | ○ | ○ | ○ | ○ | ○ | ○ | ○ |

Fig.2

| Used Liquid Medicament | Embodiment 9 | Embodiment 10 | Embodiment 11 | Embodiment 12 | Embodiment 13 | Embodiment 14 | Embodiment 15 | Embodiment 16 |
|---|---|---|---|---|---|---|---|---|
| Hydrogen Peroxide (8%) | Detenoration by 5% at 450 cycles No Functional Deterioration | Detenoration by 5% at 450 cycles No Functional Deterioration | Detenoration by 5% at 450 cycles No Functional Deterioration | Detenoration by 5% at 450 cycles No Functional Deterioration | Detenoration by 5% at 450 cycles No Functional Deterioration | Detenoration by 5% at 450 cycles No Functional Deterioration | Detenoration by 5% at 450 cycles No Functional Deterioration | Detenoration by 5% at 450 cycles No Functional Deterioration |
| Peracetic Acid (0.8%) | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Peroxide Disinfectant (10%) | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Peroxide Surface-active Agent (5%) | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Enzyme Washing Agent (10%) | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Ethylene Oxide Gas | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Iodic Disinfectant (10%) | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Alcohol Disinfectant (85vol%) | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion | No Problem with Outer Appearance and Funtion |
| Overall Judgement | × | × | × | × | × | × | × | × |

EXTERNAL COMPONENT OF ENDOSCOPE

BACKGROUND OF THE INVENTION

1. Field of the Invention

The present invention relates to an external component of an endoscope, and more precisely relates to an external component of an endoscope which is used in a portion of the endoscope which can be brought into contact with a disinfectant during a disinfecting operation after use.

2. Description of the Related Art

External components of an endoscope are made of stainless steel, plastics, or an aluminum alloy, etc. However, the portion of the endoscope, which is brought into contact with a disinfectant during the disinfecting operation after use, must be fully resistant to corrosion.

Among the material mentioned above, stainless steel or some plastics exhibit strong resistance to corrosion without being subject to a surface treatment or the like. However, an aluminum alloy must be subject to a surface treatment to obtain a resistance to the disinfectant.

To this end, the surface of the aluminum alloy base member is subject to a chromating treatment and/or an electrolytic deposition (electro deposition) in an appropriate combination (Japanese Unexamined Patent Publication No. 8-277476, No. 8-308788. No. 8-311695, etc.).

In recent years, a strong disinfectant, such as a hydrogen peroxide based liquid disinfectant has been used to prevent infection from the endoscope. If the endoscope is dipped in the disinfectant and fails to be taken out therefrom for a long time, the aluminum alloy base member which has been subjected to the conventional surface treatment can be corroded by the disinfectant, due to functional deterioration, such as a separation of the coating layer at a corner portion of the base member.

SUMMARY OF THE INVENTION

It is an object of the present invention to provide an endoscope external component having a high resistance to corrosion, in which no functional deterioration of an aluminum alloy base member occurs even if it is dipped in a disinfectant, such as a hydrogen peroxide based liquid disinfectant, for a long time.

To achieve the object, according to the present invention, an external component of an endoscope, the external component having an aluminum alloy base member, is provided, wherein the surface of the aluminum alloy base member is subjected to anodic oxidation, and thereafter, is subjected to an electrolytic deposition (electro deposition) thereon.

In an embodiment, the anodic oxidation is carried out to deposit an anodized aluminum layer whose thickness is in the range of 1–50 $\mu$m.

The thickness of the electrolytic deposition is preferably in the range of 5–25 $\mu$m.

It is preferable that the electrolytic deposition include a micro size of gel mixed therein to enhance the corrosion proof.

In an embodiment, the micro-sized gel is provided with a center core portion of 0.5–3.0 $\mu$m and has a diameter of 1.0–10.0 $\mu$m.

Preferably, the micro-sized gel is provided with a center core portion of 0.7–2.0 $\mu$m and has a diameter of 1.5–6.0 $\mu$m.

According to another aspect of the present invention, a surface preparation method for an external component of an endoscope is provided, the external component having an aluminum alloy base member. The method includes subjecting an anodic oxidation treatment to the surface of the aluminum alloy base member; and subjecting an electrolytic deposition treatment to the surface on which the anodic oxidation treatment is subjected.

The present disclosure relates to subject matter contained in Japanese Patent Application No.11-267930 (filed on Sep. 22, 1999) which is expressly incorporated herein by reference in its entirety.

BRIEF DESCRIPTION OF THE DRAWINGS

The present invention will be discussed below in detail, with reference to the accompanying drawings, in which:

FIG. 1 shows a table which represents dipping test results of eight embodiments 1 through 8 of the present invention;

FIG. 2 shows a table which represents dipping test results of eight embodiments 9 through 16 of the present invention.

DESCRIPTION OF THE PREFERRED EMBODIMENTS

Figure 3:
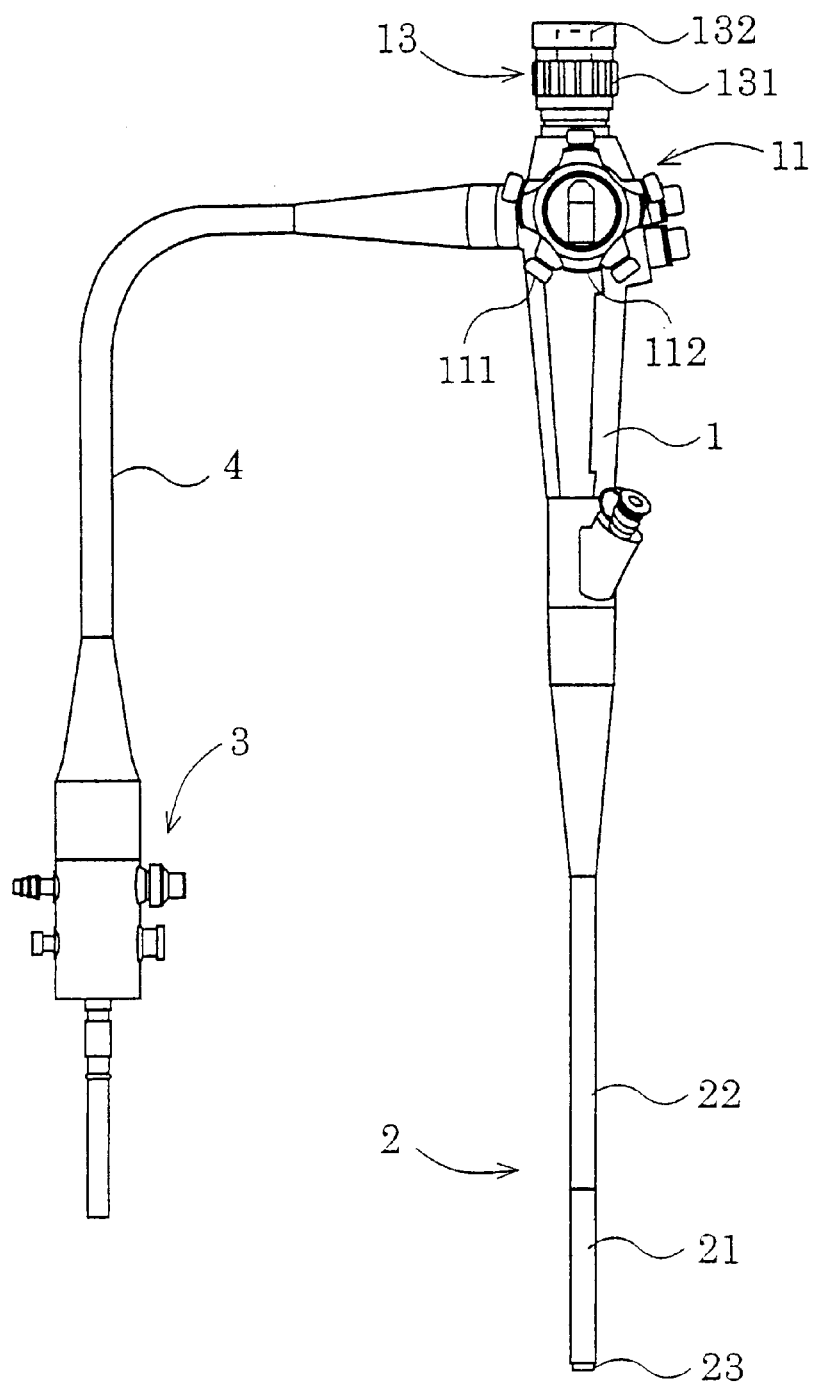
FIG. 3 is a side view of an endoscope used in the dipping tests of embodiments 9 through 16 of the invention.

FIG. 3 shows an endoscope which includes an operation portion 1 and an insertion portion 2 which is connected to the lower end of the operation portion 1. The insertion portion 2 is provided with a flexible tubular portion 22 which is provided on its distal end with a bendable portion 21 which can be optionally bent by a remote operation. An end body 23 having a view window, etc., is connected to a distal end of the bendable portion 21.

The operation portion 1 includes a bending mechanism 11 which is adapted to remotely bend the bendable portion 21, and a eyepiece portion 13 through which an enlarged object image to be viewed through the endoscope can be viewed. Some of the external components which constitute the bending mechanism 11 (e.g., diopter ring 131, eyepiece lens barrel 132, or annular members arranged inside finger abutments of the bending operation knobs 111, 112, etc.) are made of aluminum alloy based members and can be brought into contact with disinfectant during an infection operation after use. A connector 3 is connected to a light source device (not shown) and is connected to the operation portion 1 by a connecting flexible tube 4.

The external components of the endoscope made of aluminum alloy based members, which can be brought into contact with disinfectant were subjected to various kinds of surface treatment, and the tests to were made evaluate the resistance to various disinfectants including a hydrogen peroxide based liquid disinfectant, often used to disinfect the endoscope.

An anodic oxidation film can be advantageously used as an undercoating for the aluminum alloy base member, since the film is made of amorphous $\gamma$-$Al_2O_3$ and micro holes are uniformly distributed on 15 to 20% of the area of the surface of the film. Therefore, the aluminum alloy base member was subjected to anodic oxidation treatment and to electrolytic deposition to thereby increase the resistance thereof to chemicals.

As conditions common to all the embodiments, anodized aluminum in anodic oxidation was produced by the sulfuric acid method which was selected from three methods consisting of a sulfuric acid method, an oxalic acid method, and a chromic acid method, detailed below.

1) Sulfuric Acid Method:
Bath Composition: $H_2SO_4$ 150 g/l
Aluminum: 1–20 g/l
Voltage: 10–20 V
Bath Temperature: 20° C.
Electric Current Density: 1A/d $m^2$
Time: 5–40 minutes
2) Oxalic Acid Method:
Bath Composition: $(COOH)_2$: 1.0–10%
Aluminum: 1–20 g/l
Electric Current Density: 0.3–3.0 A/d $m^2$
Voltage: 80–120V
Bath Temperature: 20–30° C.
Time: 15–80 minutes
3) Chromatic Acid method:
Bath Composition: $CrO_3$: 2–10%
Aluminum: 1–20 g/l
Electric Current Density: 1.0–2.5 A/d $m^2$
Voltage: 20–60V
Bath Temperature: 20–70° C.
Time: 10–80 minutes Embodiments 1–4

In Embodiments 1 through 4, the aluminum alloy base member was degreased by a degreasing agent (e.g., "Activator" produced by Shimizu Inc.), washed with water, neutralized by an acid, washed again with water, was subjected to the sulfuric acid anodic oxidation to deposit an anodized aluminum layer (1–50 µm) on the surface of the aluminum alloy base member, was subjected to a pure-washing, and was subjected to different kinds of electrolytic deposition. Note that the layer thickness of the electrolytic deposition is in the range of 3–50 µm, and preferably in the range of 5–25 µm.

After the electrolytic deposition, the base member was subjected to a pure-washing, was subjected to air blowing, was subjected to a setting operation (i.e., the water and solvent were slowly blown away at a low temperature to clean the layer surface) at 100° C. for 20 minutes, and was subjected to baking and drying operations at 180° C. for 30 minutes.

The electrolytic deposition material used in each embodiment is as follows:
Embodiment 1: Acrylic anion type ("Elecoat AM-1" produced by Shimizu Inc.)
Embodiment 2: Fluoro-anion type ("Elecoat AMF-YT" produced by Shimizu Inc.)
Embodiment 3; Fluoro-resin anion type ("Elecoatniceron" produced by Shimizu Inc.)
Embodiment 4: Fluoro-cationic type ("CRT-1" produced by Shimizu Inc.)

Embodiments 5–8

In Embodiments 5 through 8, a micro gel (micro-sized gel) was mixed in the course of the electrolytic deposition in Embodiments 1 through 4. Embodiments 5 through 8 correspond to Embodiments 1 through 4, respectively.

The micro gel refers to, for example, acrylic melamine substance having a center core portion of 0.5–3 µm and an external shell portion of 1–10 µm (e.g., "W-2" produced by Shimizu Inc.). The micro gel can be amoeboid, spherical, or any other shape.

The size of the center core portion is preferably 0.7 to 2.0 µm and the whole diameter is preferably 1.5 to 6.0 µm. The micro gel contributes to an increase in the thickness of the corner portion of the product, in comparison with the case wherein no micro gel is used. Consequently, no deterioration, which begins at the corner portion of the product which is most greatly influenced by the chemicals, takes place.

The dipping tests were made for sample products prepared under the conditions mentioned above. In the dipping tests, the endoscopes including components corresponding to Embodiments 1 through 8 were dipped in liquid chemicals for 500 cycles at the maximum (one cycle corresponds to one hour).

In the tests, the liquid chemicals were renewed at the lapse of the service life thereof. Each time the dipping test for one cycle ended, the bent state of the fiber of the endoscope, the image, and the bending force were checked. The test results are shown in FIG. 1. In the overall judgement row shown in FIGS. 1 and 2, the symbol "○" represents usable samples for external endoscope components which are brought into contact with disinfectant, and the symbol "X" represents samples which cannot be used for external endoscope components which are brought into contact with disinfectant.

As can be seen from FIG. 1, a combination of aluminum, anodized aluminum and electrolytic deposition exhibits a high resistance to a strong disinfectant and can be used for an endoscope.

To examine the effect of the micro gel by another method, a sample having a combination of aluminum, a formation process, and an electrolytic deposition and a sample having a combination of aluminum, a formation process, an electrolytic deposition, and a micro gel formation process were compared.

Embodiments 9 through 16

In Embodiments 9 through 12, a chromating treatment was conducted as the formation process, and the electrolytic deposition was the same as that in Embodiments 1 through 4. It was found that the outcome depended upon the thickness of the layer produced by the chromating treatment and was preferably in the range of 50 Å–11000 Å, and more preferably in the range of 150 Å–3000 Å. In Embodiments 13 through 16, the above-mentioned micro gel was mixed in the course of the electrolytic deposition. The results thereof are shown in FIG. 2.

It was confirmed that the sample in which the aluminum was first subjected to a formation process, and thereafter was subjected to the electrolytic deposition or a combination of an electrolytic deposition and micro gel formation, cannot be suitably used for endoscope components which may be dipped in the disinfectant for a long time. However, the micro gel itself was useful and effective.

According to the present invention, since the surface of the aluminum alloy base member is subjected to anodic oxidation and to electrolytic deposition, even if the endoscope is dipped in a disinfectant, such as hydrogen peroxide disinfectant, for a long time, the aluminum alloy base member is highly resistant to corrosion, and thus no functional deterioration occurs.

Moreover, the mixture of the micron size gel in the electrolytic deposition layer contributes to an increase in the thickness of the coating layer at the corner portion of the endoscope component. Consequently, it is possible to prevent the coating layer from being separated at the corner portions of the component at which the functional deterioration tends to occur due to chemicals. Thus, the resistance to corrosion can be enhanced.

Although the invention has been described with reference to particular means, materials and embodiments, it is to be understood that the invention is not limited to the particulars disclosed and extends to all equivalents within the scope of the claims.

What is claimed is:

1. An external component of an endoscope, said external component comprising an aluminum alloy base member;
   wherein the surface of said aluminum alloy base member is subjected to anodic oxidation, and thereafter, is subjected to an electrolytic deposition thereon.

2. The external component of an endoscope according to claim 1, wherein the anodic oxidation is carried out to deposit an anodized aluminum layer whose thickness is in the range of 1–50 $\mu$m.

3. The external component of an endoscope according to claim 1, wherein the thickness of the electrolytic deposition is in the range of 5–25 $\mu$m.

4. The external of an endoscope according to claim 1, wherein the electrolytic deposition includes a micro-sized gel mixed therein.

5. The external component of an endoscope according to claim 4, wherein the micro-sized gel is provided with a center core portion of 0.5–3.0 $\mu$m and has a diameter of 1.0–10.0 $\mu$m.

6. The external component of an endoscope according to claim 5, wherein the micro-sized gel is provided with a center core portion of 0.7–2.0 $\mu$m and has a diameter of 1.5–6.0 $\mu$m.

7. A surface preparation method for an external component of an endoscope, said external component comprising an aluminum alloy base member; said method comprising:
   subjecting an anodic oxidation treatment to the surface of said aluminum alloy base member; and
   subjecting an electrolytic deposition treatment to the surface on which the anodic oxidation treatment is subjected.

* * * * *